(12) United States Patent
Baarman

(10) Patent No.: US 11,344,641 B2
(45) Date of Patent: May 31, 2022

(54) APPLIANCE DISINFECTION

(71) Applicant: UV Partners, Inc., Grand Haven, MI (US)

(72) Inventor: David W Baarman, Fennville, MI (US)

(73) Assignee: UV Partners, Inc., Grand Haven, MI (US)

( * ) Notice: Subject to any disclaimer, the term of this patent is extended or adjusted under 35 U.S.C. 154(b) by 0 days.

(21) Appl. No.: 17/418,040

(22) PCT Filed: Dec. 23, 2019

(86) PCT No.: PCT/US2019/068289
§ 371 (c)(1),
(2) Date: Jun. 24, 2021

(87) PCT Pub. No.: WO2020/146137
PCT Pub. Date: Jul. 16, 2020

(65) Prior Publication Data
US 2022/0031883 A1 Feb. 3, 2022

Related U.S. Application Data

(60) Provisional application No. 62/789,254, filed on Jan. 7, 2019.

(51) Int. Cl.
*A61L 2/10* (2006.01)
*A23L 3/28* (2006.01)
(Continued)

(52) U.S. Cl.
CPC .................. *A61L 2/10* (2013.01); *A23L 3/003* (2013.01); *A23L 3/28* (2013.01); *A61L 2/03* (2013.01);
(Continued)

(58) Field of Classification Search
CPC ....... A23L 3/28; A23L 3/003; A23V 2002/00; A61L 2/10; A61L 2/03; A61L 2202/11;
(Continued)

(56) References Cited

U.S. PATENT DOCUMENTS 6,524,529 B1 2/2003 Horton, III
7,372,044 B2 5/2008 Ross
(Continued)

FOREIGN PATENT DOCUMENTS

GB 2 421 217 6/2006
WO 2019/190967 10/2019
WO 2019/241112 12/2019

OTHER PUBLICATIONS

International Search Report and the Written Opinion of the International Searching Authority for International Application No. PCT/US2019/068289 dated Apr. 27, 2020.

*Primary Examiner* — Kiet T Nguyen
(74) *Attorney, Agent, or Firm* — Warner Norcross + Judd LLP

(57) ABSTRACT

An appliance disinfecting device with monitoring and safety interlock system that utilizes user detection and sensors to detect touch and can provide user feedback and decorative features. The device can include a UV transmissive material that provides disinfection of hard to reach surfaces or areas safely. The appliance disinfection device can include an automatic interlock to protect a user from UV exposure. The optics used for the UV disinfection allow the device to become a human interface. The device can be connected to the appliance control system which can be connected to a network and cloud interface.

10 Claims, 7 Drawing Sheets

(51) Int. Cl.
*A23L 3/00* (2006.01)
*A61L 2/03* (2006.01)

(52) U.S. Cl.
CPC ....... *A23V 2002/00* (2013.01); *A61L 2202/11* (2013.01); *A61L 2202/122* (2013.01); *A61L 2202/14* (2013.01); *A61L 2202/23* (2013.01)

(58) Field of Classification Search
CPC ........... A61L 2202/122; A61L 2202/14; A61L 2202/23
USPC .................................................... 250/455.11
See application file for complete search history.

(56) References Cited

U.S. PATENT DOCUMENTS

| | | |
|---|---|---|
| 8,431,910 B1 | 4/2013 | Perry |
| 8,481,970 B2 | 7/2013 | Cooper et al. |
| 9,066,987 B2 | 6/2015 | Bettles et al. |
| 2008/0256741 A1 | 10/2008 | Garcia et al. |
| 2009/0218512 A1 | 9/2009 | Ranta et al. |
| 2013/0234041 A1 | 9/2013 | Deal |
| 2013/0243647 A1 | 9/2013 | Gamer |
| 2013/0270445 A1 | 10/2013 | Gaska et al. |
| 2014/0061509 A1 | 3/2014 | Shur et al. |
| 2015/0165079 A1 | 6/2015 | Shur et al. |
| 2016/0036952 A1 | 2/2016 | Kim et al. |
| 2016/0045633 A1 | 2/2016 | Pagan et al. |
| 2017/0286651 A1* | 10/2017 | Erhart .................... B25J 13/006 |
| 2018/0132697 A1 | 5/2018 | Des-Kalyanam |
| 2019/0262526 A1* | 8/2019 | Wyeth ................... A61M 1/288 |

* cited by examiner

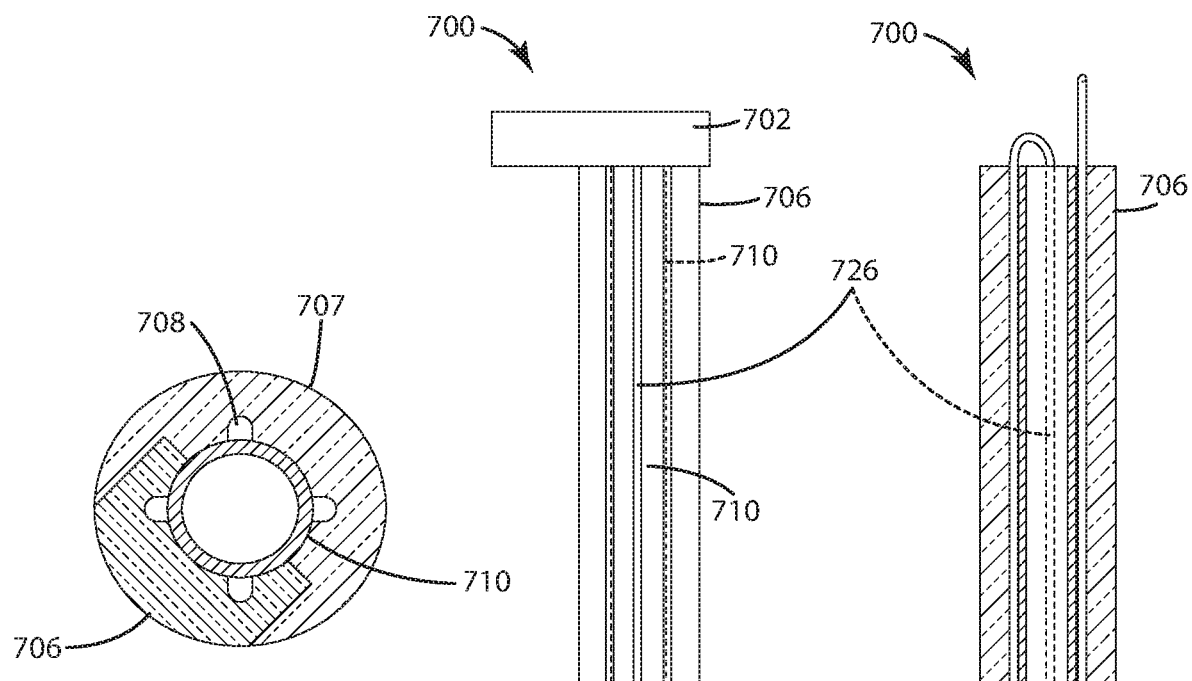
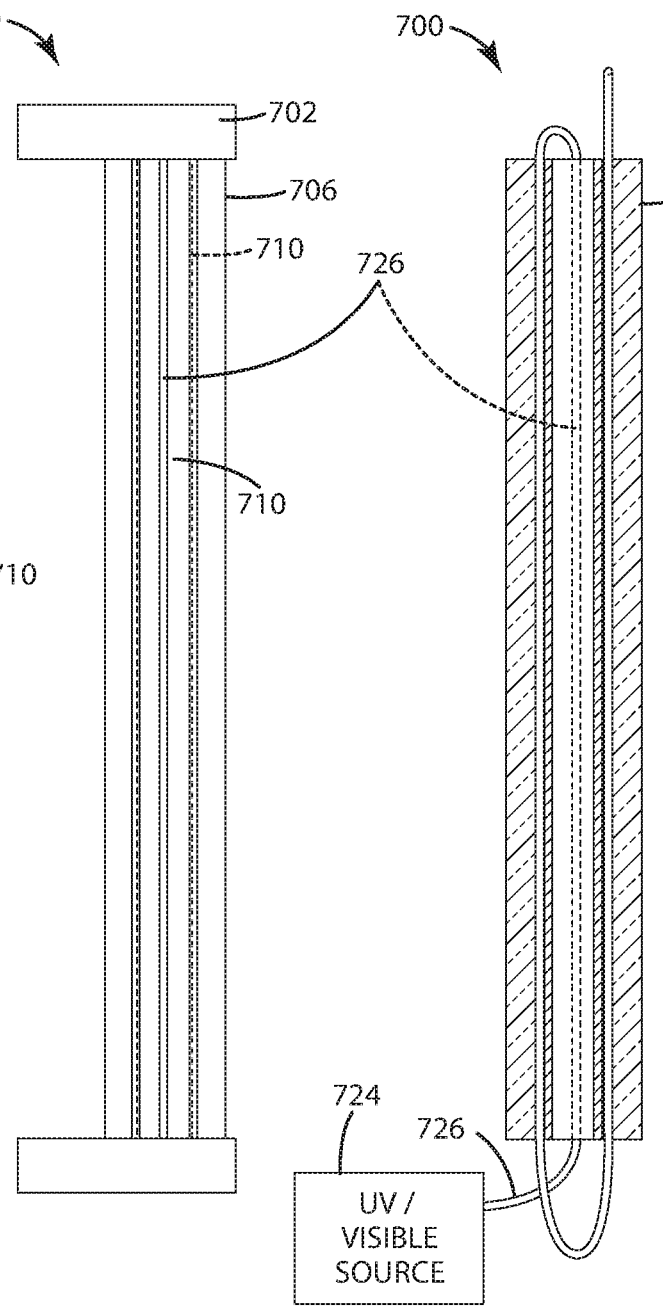
Fig. 7A
Fig. 7B
Fig. 7C

APPLIANCE DISINFECTION

CROSS-REFERENCE TO RELATED APPLICATION

This patent application is related to U.S. patent application Ser. No. 17/418,044 to David W Baarman, filed Jun. 24, 2021, entitled "Transportation Disinfection".

FIELD OF THE INVENTION

The present disclosure relates to the field of disinfection, and more particularly toward disinfecting aspects, components, or surfaces of appliances while protecting users from UV.

BACKGROUND

Infection by a foreign organism, such as bacteria, viruses, fungi, or parasites, can be acquired in a variety of ways. But once acquired, the infection, if harmful, may colonize and result in illness. The immune system of the infected host, e.g., the person, may react to the infection and attempt to kill or neutralize the foreign organism. However, in some cases, the immune system may be insufficient to completely neutralize the infection, and hospitalization may be necessary for survival. For these and other reasons, infectious disease prevention is conventionally preferred over reliance solely on the immune system of the infected host.

Conventional efforts to prevent spread of infectious disease often involve manual disinfection techniques, such as wiping down or washing surfaces that may harbor foreign organisms. Because infectious diseases can be spread in a variety of ways, such as via direct contact from person to person, manual disinfection techniques can be time and labor intensive. For example, indirect contact from an infected person to an environmental feature and then to another person who contacts the contaminated environmental feature is a common mode of infection. Because there are numerous surfaces in the environment, it is considered laborious and time intensive to decontaminate all or substantially all surfaces in the environment, essentially making such decontamination impractical in many cases. As another example, air borne pathogens from an infected person can make their way into areas that are inaccessible to manual disinfection techniques.

The appliance environment includes many surfaces that can become contaminated, which can be labor intensive to manually decontaminate due to the number and variety of surface (e.g., nooks and crannies). Storage compartments in a refrigerator are particularly labor intensive to decontaminate, potentially involving removal of food stored within. Additionally, or alternatively, in heavily used appliances such as refrigerators, dishwashers, tablets, smart phones or other appliances with screen based user interfaces, the frequent number of interactions increases the likelihood of surface contamination, again increasing the labor and time to effectively decontaminate such surfaces with conventional techniques. For these and other reasons, conventional techniques fail to enable decontamination of appliance environments in a practical manner.

In other realms, conventional disinfection systems have involved application of UV light within an enclosed space to protect the user from significant exposure to the UV light. For instance, a target device, such as a dental instrument or surgical instrument, may be stored in a box to protect the user from UV. The mechanical isolation of the target device may be used for safety while over dosing the product with UV light for fast disinfection. Other conventional systems may utilize UV wands and allow portable disinfection by moving the UV wand over a surface. However, disinfection with a UV wand often leads to incomplete disinfection because the dosing amount is substantially controlled by the human operator of the UV wand. Additionally, it is noted that many conventional UV disinfection constructions utilize high intensity application of UV light, which restricts the size of a UV light source to a small or high cost source due to the high power lamps and drivers.

Some known appliance disinfection systems exist, but with major limitations. Reaching the full surface area of the appliance is one issue while being safe to use in a human filled environment is also an issue. Some known appliance disinfection systems are limited to specific materials and focus on direct application of light for disinfection. These known disinfection systems often are configured to deliver more UV to enable reaching as much surface area as possible of a device. Further, some known solutions for disinfecting food require direct exposure and do not provide storage solutions. Common packages and storage containers limit or prevent exposure. Problems of known disinfection systems also relate to the impact of UV energy on devices. The previous directive of more is better has negative ramifications to the destruction of materials not intended for intense UV exposure. Further, known solutions lack an automated process for safely providing disinfection.

SUMMARY OF THE INVENTION

The present disclosure in accordance with one embodiment provides enhanced decontamination of surfaces or zones in an appliance environment, potentially yielding better decontamination results over conventional techniques. The present invention provides solutions to problems related to disinfection or treatment in an appliance environment or improves a disinfection or treatment process to provide additional benefits. Many aspects of the present invention incorporate disinfection or treatment into appliance workflow to increase its attractiveness to the user.

In one aspect, treatment can be halted or otherwise controlled in response to operation of an interlock between an appliance and appliance compartment. In one embodiment, an appliance includes a power distribution system mounted to an appliance and a moveable compartment, such as a drawer, that includes a treatment device capable of being powered by the power distribution system when the drawer is positioned proximal the power distribution system. The power distribution system acts as an interlock in that movement of the drawer that breaks, disrupts, or limits the power link between the power distribution system and the treatment device can interrupt or halt an ongoing disinfection cycle. This can also be used to prevent a disinfection cycle from beginning. Further, it can trigger scheduling of a disinfection cycle in the future, for example, once the interlock is re-established by the compartment being moved back into position to establish the link with the power distribution system.

In one embodiment, the moveable compartment can be an appliance drawer, for example a crisper drawer of a refrigerator that stores fruits and vegetables. The treatment device can be mounted to the drawer. Wireless power from a wireless power supply mounted to the appliance can be provided while the drawer is in a closed position, for example through inductive power transfer or contact-based power transfer. The power/communication can be provided to the treatment device, which can output UV light for treatment of the compartment surfaces and contents of the compartment. When the drawer is opened, the movement breaks the wireless power link. The treatment device can be easily clipped to the interior of the crisper drawer, as an example, for a simple integration that is elegant and easy to manufacture.

In one embodiment, the treatment device provides multi-spectrum UV light for both disinfection and food preservation. The treatment device can be controlled according to a treatment protocol. For example, operation of the treatment device can be halted or prevented in response to certain triggers and operation of the disinfection device can be started or scheduled for certain types and dosages of UV light, for example UV-A/B and UV-C, based on particular triggers. For example, operation of the treatment device can be halted or prevented or certain types and dosages of UV light can be provided in response to particular triggers, such as an appliance interlock being broken or re-established, an appliance drawer being opened or closed, or a control system indicating an appliance compartment has been opened or closed a certain period of time. The disinfection protocol can include halting, preventing, initiating, or scheduling a low dose UV-C cleaning cycle, a high dose UV-C cleaning cycle, or a UV-A/B food preservation cycle in response to any one or combination of suitable triggers. The treatment device may include multiple UV lighting sources, such as a UV-C source for disinfection and a UV-A/B lighting source for food preservation, for example by generating photosynthesis within fruits and vegetables. The UV-A/B lighting source can provide a food preservation cycle that does not stimulate food in the appliance compartment too much by dosing a very limited dose and limiting the dose to a timed sequence. That is, the UV-A/B dosage and timing can be set such that it is sufficient for photosynthesis in the fruits and vegetables in the appliance compartment without overstimulation. For example, a UV-A/B food preservation dose could be provided with a certain range of 30 mW/m$^2$ for 15 minutes every two hours when the system has not been tripped by user interaction. The treatment protocol can also scale or be controlled based on when new food product enters the appliance. For example, UV treatment dosing can be very minimal when new food product enters the appliance and at specific timed intervals thereafter.

In one embodiment, a food storage compartment can be manufactured from a fluoropolymer such as plastic injected PerFluoroAlkoxy (PFA) or Teflon to facilitate UV-C transmission. The thickness of the walls of the food storage compartment can be selected to provide particular UV transmissive characteristics. A thinner wall can provide better UV transmissive characteristics, e.g., UV light travels farther along all of the food storage compartment surfaces. By using a thickness of 2-12 mills a structural enclosure and sizes may dictate thickness for structure can be provided. In some embodiments, the food storage compartments are bags. For example, the bags can be 1.5-2 mil for storage and may have a zipper seal and ventilation, depending on use or application. The enclosures can be tailored to hold fruit, eggs or other produce in specific orientations to assure proper dosages much like an egg carton, but clear. The inner surfaces of the food storage compartment can be textured to allow scattered reflection of UV light. The inner surfaces of the food storage compartment may also be coated with a reflector to protect the appliance from UV exposure and also provides a good dispersion and reflection of the UV light, for example, dispersion and reflection characteristics that allow UV light to relatively uniformly reach the different areas within the food storage compartment. The surface can be both coated with a reflective coating and be textured. The food storage compartment walls enable light-piping within the appliance and enables food being stored to be treated effectively.

In another aspect, capacitive touch sensors can establish a first touch range and a second accurate touch zone. A capacitive touch sensor can detect proximity quite far. For example, some capacitive touch sensors can proximity sense up to about 30 cm away from the sensor. However, these capacitive touch sensors are typically not used at these longer z ranges (e.g., greater than 5 cm-15 cm) because they cannot accurately define an x/y position at those distances. A capacitive sensor system can be configured to detect proximity at a longer distance (e.g., greater than 30 cm) to turn off or prevent operation of the treatment device, and then a specific locational touch range can be provided within typical touch ranges (e.g., less than 30 cm).

In another aspect, cross flow disinfection of a human interface device touch screen can be provided. For example, an appliance, such as a tablet, smart phone, or refrigerator, may include a human interface device touch screen or touch interface. By projecting UV from one or multiple sides, the surface can be treated with a suitable UV-C dose to remove bacteria and pathogens. In one embodiment, a UV-C source is disposed behind the display or surface near an edge of the surface. A UV-C transmissive lens can be positioned to slightly overlap the touch screen or interface in order to project the UV-C across the surface. A reflector can partially surround the lens and UV source to project the UV light across the surface. The lens and reflector cooperate to keep the bulk of UV energy along the human interface surface and reduce or minimize user exposure to the UV. In one embodiment, DOWSIL MS-1003 can be used for the lens material along with other moldable materials and quartz.

In yet another aspect, an appliance may include a disinfection device incorporated into an appliance handle. The disinfection device can disinfect the handle surface as well as provide decorative features and feedback to the user. The appliance handle can provide a mechanically strong handle that includes a disinfecting surface. The surface can be lit with decorative lighting and allow UV-C disinfection. The disinfection device in cooperation with the handle can provide a human interface device that can track touches, movement, force, and allow feedback such as warnings, error states, and arriving stations as a few examples. Handles may be wrapped in fiber or light-piped to light logos or provide various lighting design details that are highly decorative and yet functional for disinfection.

In yet another aspect a UV disinfecting module with haptic, and visual feedback, capacitive touch and communications for ease of control and independent safety monitoring and interlock control is provided. It can be controlled and monitored with a simple communications interface for decorative colors and intensity configuration. This module can turn almost any surface into a multifunctional human interface device.

An appliance may be provided with a film or transmissive surface treatment to facilitate UV transmission. For example, in one embodiment UV transmissive materials may be used to treat displays or surfaces. For example, the treated surface may be an appliance work surface, an appliance food preparation or storage area, or an appliance handle. There are a variety of use cases for the UV transmissive surface treatment including at least:

a UV source lighting through a film material from the side that is directed to the surface display;

a UV source from below the appliance surface transmitting UV through a transmissive material;

a UV source above and below where the UV source on the supporting material transmits UV through the transmissive supporting material allowing the bottom to be disinfected properly;

a UV source above where the UV source disinfects the appliance surface by first radiating on the device and secondarily transmitting UV through supporting material transmits UV through the transmissive supporting material allowing the bottom or side to be disinfected properly—dependent on mounting;

a UV source disinfecting a case around the appliance surface wherein the case distributed the UV to areas around the appliance surface for proper disinfection; using DOWSIL MS1003.

Food borne pathogens and bacteria can be eliminated on surfaces and reduced on food through treatment and limited dosage. Appliances can use this technology to better protect consumers and prolong the life of fruits and vegetables. This process can also limit smells and provides cleaner surfaces by limiting bacterial growth. Further, by automating the treatment systems, faster and more controlled disinfection and charging solutions can be provided that also provide better customer satisfaction. In addition, the material solutions for appliance surfaces allow UV-C patterns to be projected creating specific areas for bacterial and pathogens to be destroyed. The embodiments of the present invention can provide mechanical and material solutions that enable 3D disinfection. Use of UV transmissive materials for food storage and preservation addresses many problems. Further, sensors and control interlocks address problems with existing disinfection solutions. Some embodiments of the present invention also relate to UV transmissive materials and usage. Designing appliance surfaces that enable treatment of what was previously a blind surface of the device can now enable 3D disinfection. The additional automatic safety monitoring and interlock provides a user interface that enables user understanding of the process including disinfection status. This can enable automated charging and disinfection while protecting the user and providing a user interface. Appliances that store or prepare food become ideal for these disinfection solutions. Providing a workspace to provide food that is disinfected is also valuable. Examples of ideal appliances include but are not limited to refrigerators, microwaves, cutting and food preparation surfaces, ranges, and any appliances with touch controls. It should also be noted that best practice is to use the UV source for as many disinfecting options as possible to limit cost. One UV source can be utilized to disinfect multiple areas. For example, for a crisper we may use a small handle or drawer pull that is in contact with the UV light and cleans the external handle while cleaning the internal surfaces. Thus the contaminated handle is cleaned as well providing a multipurpose use of the same source.

BRIEF DESCRIPTION OF THE DRAWINGS

FIGS. 7A-7C illustrate an appliance handle with disinfection, user feedback and decorative lighting.

DESCRIPTION OF THE INVENTION

Figure 1:
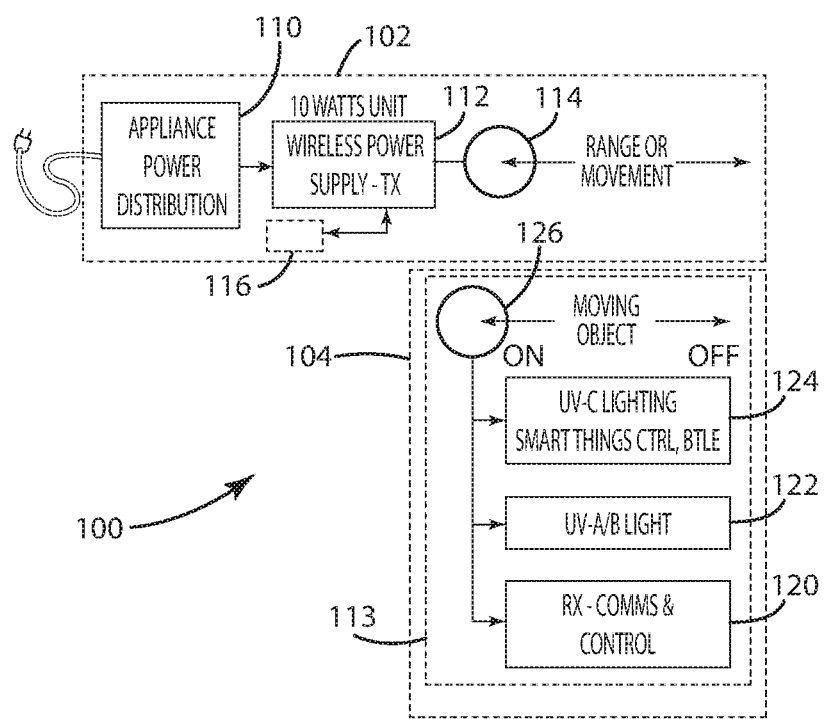
FIG. 1 illustrates one embodiment of an appliance interlock.

A disinfection system in accordance with one embodiment is provided in the illustrated embodiment of FIG. 1 and designated 100. The disinfection system 100 may include a first portion 102 and a second portion 104, also described herein respectively as a power connection portion and a linked portion. In one embodiment, the power connection portion 102 is a stationary portion, and the linked portion 104 is a movable portion; however, the present disclosure is not so limited. In one embodiment, the first portion 102 and the second portion 104 are separable or provided in separate housings. Alternatively, the first portion 102 and the second portion 104 may be integral such that the first portion 102 and the second portion 104 are provided in the same housing or device.

In the illustrated embodiment, the first portion 102 includes an appliance power distribution interface 110 configured to receive power from an external source. Optionally, the external interface includes a communication interface to facilitate communication with one or more external devices. The first portion 102 may be a first portion power link 114 operable to supply power to a second portion power link 126 of a second portion 104. Together, the first and second portion power links 114, 126 may form a system power link that facilitates transference of power from the external source to the second portion 104 to power a control system 120 and the UV light sources 122, 124 of the treatment system 100. The system power link in one embodiment may be a connectionless power link, such as a wireless power link.

The second portion 104 in the illustrated embodiment includes the control system 120 and the UV light sources 122, 124. It should be understood, however, that the present disclosure is not so limited. For instance, the control system 120 or aspects thereof may be disposed in the first portion 102. The UV light sources 122, 124, as discussed herein, may be optically coupled to a transmissive element (not shown in FIG. 1) to facilitate delivery of UV light energy to a treatment zone.

The control system 120 of the treatment system 100 may include circuitry operable to direct operation of the UV light sources 122, 124, and may include one or more sensors configured to provide sensor information. As an example, the sensor information provided by the one or more sensors may be indicative of a human usage condition with respect to a device, surface, or disinfection zone, or a combination thereof, that is associated with the treatment system 100. The device or disinfection zone in one embodiment described herein may be a component or associated with such a component in the realm of appliance (e.g., a human interface of an appliance). The control system 120 may be configured to discontinue application of UV light energy to the disinfection zone in response to the human usage condition being indicative of a human body part being in proximity to or potentially in proximity to the treatment zone. In one embodiment, the control system 120 may discontinue application of UV light energy within 1 s or less of detecting a human body part in proximity to the disinfection zone.

The control system 120 may be operable to detect or determine an amount of UV dosage (e.g., irradiance mW/m^2*exposure time s) provided to the disinfection zone and control decontamination of the same based on the amount of UV dosage. Such detection and control may be adaptive based on sensor information indicative of UV dosage to the disinfection zone; alternatively, the detection and control may be estimated based on one or more predetermined parameters (e.g., intensity of the UV light source and transmission effectiveness of the transference element).

The control system 120 may be operable to provide feedback to a human in a variety of ways, indicating a variety of conditions, one or more of which may pertain to decontamination of the disinfection zone. Examples of feedback include haptic feedback, visual feedback, and audio feedback.

To provide a more specific example, the disinfection zone may be associated with a refrigerator drawer or appliance handle. The control system 120 may control operation of the UV-C source 124 to disinfect a human interface portion of the refrigerator door or appliance handle, and may present visual feedback in the form of light having a spectrum different from the UV light to indicate decontamination is complete or underway. For instance, the visual feedback may be a red light provided to the same transmissive element as the UV light from the UV light source 124 such that the color of the transmissive element as seen by the human is sufficiently distinctive to indicate decontamination is underway. The control system 120 may also control operation of the UV-A/B source 122 to treat food, such as fruits and vegetables, in a storage compartment.

In one embodiment, the control system 120 may be configured for operator detection. Using motion, acceleration, capacitance touch or power feedback or inputs, the controller may determine a user is present and shut off UV disinfection.

In one embodiment, the control system 120 may provide motion interlock capabilities and capacitive presence-based capabilities, or both. In one embodiment, motion may be detected using infrared. Additionally, or alternatively, acceleration sensors may provide output indicative of a hand having reached in with respect to the device and when the device is moved, tapped or manipulated. Capacitive proximity sensing may also facilitate identifying touches, and provided to the control system 120 as a basis for tracking touches and specific buttons within the plastic and transmissive surfaces of the system.

FIG. 1 illustrates one embodiment of a treatment device for an appliance that includes a power interlock. The depicted embodiment includes a power interlock that includes a wireless power supply transmitter 112 installed in an appliance 102 and a wireless power receiver 113 installed in a moveable object 104, such as an appliance compartment, drawer, or food storage container. Movement of the moveable object 104, for example by opening an appliance drawer or removing a food storage container, can disable the power to the wireless receiver 113. The transmitter 112 can be configured to communicate with an appliance communication system 116, for example an appliance bus, to provide information relating to temperature, light, disinfection cycles, maintenance, or other information relating to operation of the treatment device. The transmitter coil 114 and the receiver coil 126 can be disposed on the appliance 102 and moveable object 104 respectively to enable power transfer and communication while the moveable object 104 is positioned within proximity of the appliance, for example where the drawer is closed or a food storage compartment is installed in the appliance near the wireless power supply transmitter coil 114. The wireless power system 112, 113 provides function and interface with the disinfection area—for example, the internal surfaces and space within the moveable object 104. Where the moveable object 104 is a drawer, the drawer can disconnect the power from the transmitter 112 and shut off the disinfection cycle either by way of breaking the power link provided by the power interlock or alternatively by the receiver side controller 120 (e.g., in response to instructions from the appliance or a disinfection protocol). The disinfection device, for example a controller on the appliance or moveable object, can track interactions with the moveable object, for example by monitoring the status of the power interlock, to trigger or otherwise schedule a cleaning cycle where the UV can be operated to disinfect or otherwise treat the moveable object. This and other sensor data can be relayed to the transmitter 112 and then to the appliance control and data bus 116.

Figure 2:
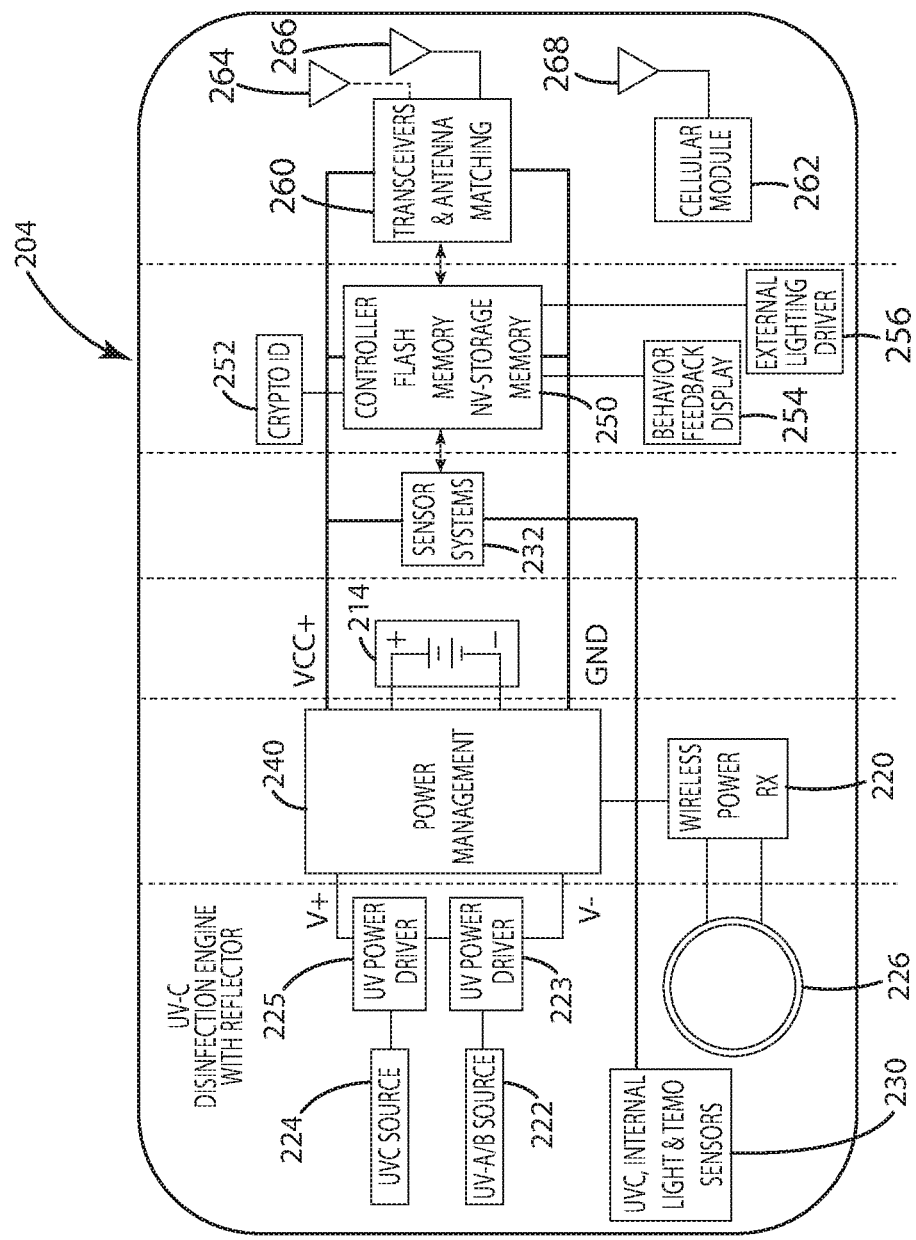
FIG. 2 illustrates one embodiment of a UV disinfection engine.

Turning to the illustrated embodiment of FIG. 2, the second portion 104 of the disinfection system 100 is shown in further detail in accordance with one embodiment of the present disclosure. A block diagram of circuitry for a UV disinfection engine for a receiver or treatment device that may be surrounded in a protective enclosure or moveable object 204 is depicted. The receiver 113 may include a UV-C disinfection engine. The treatment device 113 may be installed on an object 204 that includes a reflector and UV transmissive material for assisting in transmitting UV from the treatment device to the various surfaces of the object or items disposed within the object.

The treatment device may include a controller 250 that can control operation of the treatment device, including circuitry associated with the UV disinfection engine. The controller can be coupled with various circuit components, directly or indirectly, throughout the treatment device. For example, the controller can be coupled to various sensor systems 230 that can provide information regarding temperature, capacitive touch, USB input, UV-C intensity, light, movement/acceleration, or other information, a power management system 240 that can drive UV sources, a heavier feedback display 254, external lighting driver system 256, a crypto ID circuit 252, along with various transceivers and antenna circuitry 260.

The controller 250 can include any and all electrical circuitry and components to carry out the functions and algorithms described herein. Generally speaking, the controller 250 may include one or more microcontrollers, microprocessors, and/or other programmable electronics that are programmed to carry out the functions described herein. The controller 250 may additionally or alternatively include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware. Such components can be physically configured in any suitable manner, such as by mounting them to one or more circuit boards, or arranging them in other manners, whether combined into a single unit or distributed across multiple units. Such components may be physically distributed in different positions in the disinfection system 100, or they may reside in a common location within the disinfection system 100. When physically distributed, the components may communicate using any suitable serial or parallel communication protocol, such as, but not limited to: CAN, LIN, FireWire, I2C, RS-232, RS-422, RS-485, SPI, Ethernet, Universal Serial Bus (USB), RF cellular, WiFi, Bluetooth, or Bluetooth Low Energy.

The onboard sensor system 23 may include a variety of different sensors and may be coupled to a variety of additional sensors 230. The sensor system 232 or additional sensors 230 may include a haptic feedback device for indicating when the moveable object 204, for example a drawer or storage, should be checked. That is, the controller 250 may operate according to a disinfection protocol that can utilize haptic feedback to urge a user to move the moveable object 204. This can be helpful to shift the position of the moveable object or, where the moveable object is a compartment to shift the objects stored in the compartment to ensure that the disinfection cycle causes UV light to scatter, reflect, and be transmitted to the various surfaces and nooks and crannies around the moveable object. The haptic feedback itself can cause slight variations in the positioning of the moveable object or its contents sufficient to change the disinfection coverage area or alternatively can prompt a user to interact with the moveable object, which can shift the position and interface of the UV source with respect to the object.

The object 204 may include a behavior feedback display that includes a lighting controller and a plurality of lights for providing behavior feedback to a user, and the feedback can be informative regarding the various disinfection features, decorative feedback, or feedback related to the appliance features. For example, where the object 204 is a handle, different messages can be provided to the user by changing the color of the decorative lighting associated with the behavior feedback display. For example, light pipes surrounding the outside of the handle can indicate the temperature is low in the refrigerator or freezer by changing the color of the lighting surrounding the handle. The status of the door can be indicated, for example if the refrigerator or freezer door is left ajar the color of the handle can be changed to a particular color or the behavior feedback controller can flash or otherwise operate the lighting in a particular pattern to inform the user. As yet another example, the behavior feedback display can provide a particular feedback lighting display if certain maintenance should be performed or replacement parts should be ordered, e.g., to inform a user that the water filter end of life is approaching or has passed.

The controller 250 may include or be coupled with various different types of memory. For example, the controller 250 may include non-volatile memory for tracking power/interlock cycles by setting a flag before power down. The controller 250 may include volatile and and/or non-volatile storage memory. For example, the controller may include flash memory. The operation of the controller and related UV disinfection circuitry can be implemented or adapted partially or in full as described in U.S. provisional patent application 62/650,340, entitled Disinfection Behavior Tracking and Ranking, filed on Mar. 30, 2018 to Baarman, which is hereby incorporated by reference in its entirety.

The object may include a wireless power receiver controller 220, or alternatively the controller 250 may be utilized as a wireless power receiver controller. The wireless power receiver controller 220 includes circuitry to feed and, if appropriate, condition power for the power management system 240. In the current embodiment, the wireless power receiver 220 received inductive power from a coil 226. In alternative embodiments, the wireless power receiver 220 may be coupled to a pair of contacts that provide direct electrical contact to a contact-based wireless power transmitter.

The power management system 240 can control and manage power for the receiver 113. The power management system can charge an optional rechargeable battery 242 with power provided from the wireless power receiver 220. The power storage 242 can be sized for dose and interval of typical use. The power management system can also draw power from the optional rechargeable battery to provide power to the various circuitry on the receiver 113. The power management system 240 can also provide power to the UV power drivers 223, 225 that are coupled with the UV-C source 224 and UV-A/B source 222. The power management system 240 can also provide VCC+ to the various circuit components throughout the object, such as the various sensor systems, the controller 250, and the various transceivers and antenna circuitry 260. The power supply can produce a regulated power source when voltage from the battery is present. The system can be recharged wirelessly.

In the illustrated embodiment of FIG. 2, the UV light sources 222, 224 may receive power from a single or separate set of UV drivers 223, 225, which may be configured to receive power from the power link created by the wireless power receiver coil 226 under direction of the wireless power receiver controller 220, power management system 240, and the receiver controller 250. The UV light sources 222, 224 may be monitored via one or more UV sensors 230 by the control system 250 to facilitate control of operation of the UV light sources 222, 224 to perform disinfection or other treatment procedures. The UV sensor can provide type and intensity information and can track that information over time or provide the information to the control system 250 for tracking. Non-volatile storage can store accumulated information received by the controller 250. The UV light sources 222, 224 may be any type of sources capable of generating UV light. The UV-C source may generate UV-C light for disinfection purposes, while the UV-A/B source may generate UV-A/B light for generating photosynthesis in fruits and vegetables. Example constructions of the UV light sources 222, 224 include cold cathode light, a low-pressure Mercury light, or a UV-C LED, each of which convert electrical power into UV radiation. The UV sources can be configured for direction toward a surface or set of surfaces, such as an appliance. In some embodiments, the UV sources 222, 224 may include a ballast. A reflector can be configured to direct the UV toward specific areas, for example to flood a specific area that may otherwise be difficult to reach with UV light without the reflector in place.

The disinfection engine of the object 204 can include a crypto ID 252 for system security, communications, and updates. The crypto ID circuit 252 can also enable communications for tracking and data collection to enable data analytics.

The controller 250 can be a low current microprocessor on a regulated rail. The controller can monitor temperature (ambient, source, and microprocessor). It may also monitor an accelerometer, capacitive, and voltage sensors. The module can also allow external communicates and interface, as well as enable lighting control for user feedback.

The object 204 may include a storage capacitor sized to enable a non-volatile memory write before power down, for example the storage capacitor may be included in the controller circuitry 250 or coupled to the controller circuitry. A preset voltage threshold can interrupt and inform the microprocessor to shut down all high current systems and the remaining energy can be used to write to non-volatile memory for an interlock cycle flag. Upon power up that flag can trigger initiation or scheduling of a disinfection cycle.

The transceivers and antenna matching circuitry 260 can include WiFi, BTLE, BTLE Industrial, 400 or 900 MHz modules as an example. BTLE may provide monitoring for devices. A cellular module 262 may be provided for advanced hub use. The antennas (mesh/WiFi antenna 264, BTLE antenna 266, cell antenna 268) may be optionally routed to outside ambient or external as shown or chip type antennas on the PCBA.

Figure 3:
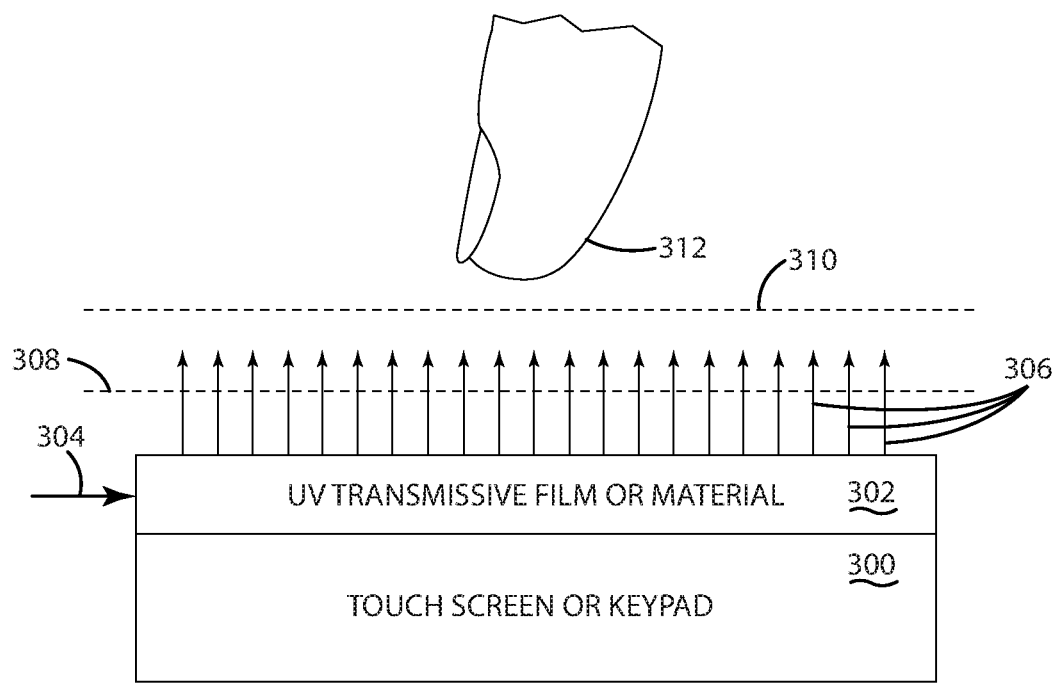
FIG. 3 illustrates a representative view of a UV transmissive material for an appliance.

FIG. 3 shows an appliance 300 that includes a touch screen or keypad along with a capacitive or other sensor. A UV transmissive film or material 302 is coupled or positioned adjacent to the touch screen or keypad for assisting in transmitting UV energy for disinfection of the user interface. The UV transmissive material 302 accepts UV light 304 (for example from a UV-C source) and disperses the UV light 306 across the material to disinfect the touch surface 302, 300. In the current embodiment, the capacitive sensor included in the appliance 300 is configured with a first capacitive gross touch zone 310 for triggering a UV interlock and a second, specific touch area 308 for keyboard entry. That is, the capacitive sensor can be configured in conjunction with a controller in the appliance to shut off or prevent UV disinfection if a finger 312 passes a capacitive sensor value associated with the first safety threshold 310. In addition, the capacitive sensor can also identify the finger passing a conventional capacitive touch threshold for operation or the touch screen or keypad. The z distance associated with the first safety threshold is larger than the z distance associated with the capacitive touch threshold. In the current embodiment, the UV disinfection cycle can be halted in response to a finger 312 passing the first safety threshold 310 such that an appreciable amount of UV light does not reach the user's finger during operation of the touch screen or keypad on the appliance 300.

The UV-C transmissive materials can be utilized in connection with a UV source lighting through a film material from the side that is directed to the surface display. The transmissive materials can be utilized with a UV source from below the appliance surface transmitting UV through a transmissive material. The UV transmissive materials can be utilized with a UV source above and below where the UV source on the supporting material transmits UV through the transmissive supporting material allowing the bottom to be disinfected properly. The UV transmissive materials can be utilized with a UV source above where the UV source disinfects the appliance surface by first radiating on the device and secondarily transmitting UV through supporting material that transmits UV through the transmissive supporting material allowing the bottom or side to be disinfected properly. The UV transmissive materials can be utilized in conjunction with a UV source disinfecting a case around the appliance surface wherein the case distributed the UV to areas around the appliance surface for proper disinfection. In one embodiment, the UV transmissive material can be DOWSIL MS1003, available from Dow Chemical.

Figure 4:
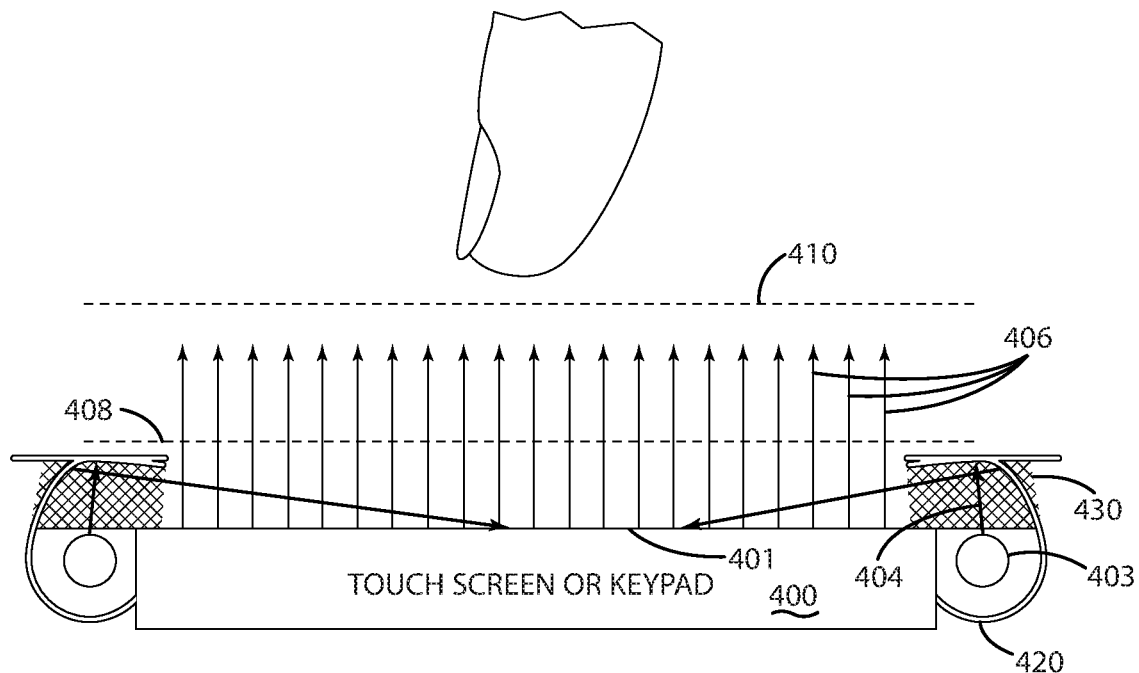
FIG. 4 illustrates a representative view of a UV treatment device for an appliance utilizing a transmissive lens and reflector.

FIG. 4 shows a touch surface or keypad 400 using a cross flow driven solution. Output from the UV-C source 403 is driven across the surface 401 of the touch screen or keypad 400. In this embodiment, the UV-C source or sources 403 and the reflector or reflectors 420 are configured at almost parallel angles protecting the consumer from exposure to the UV. A bezel is configured to shield the UV-C and recess the screen behind a UV-C transmissive lens 430 to limit consumer exposure to UV. This form of appliance touch screen or keypad direct surface treatment provides a low profile UV-C. Just as in the FIG. 3 embodiment, a first capacitive gross touch zone 410 for triggering a UV interlock can be provided along with a second specific touch area or threshold 408 for keyboard entry or otherwise interacting with the user interface 400.

The UV source 403, transmissive lens 430, and reflector 420 cooperate to direct the UV energy across the surface of the appliance 400. As depicted, much of the UV energy can be directed across the plane of the appliance surface to provide disinfection. The UV energy is reflected and supplied to the surface at acute angles relatively close to parallel with the surface. Further, to the extent the appliance surface 400 is not uniform, the various UV energy provided at varying angles by the reflector and transmissive lens can reach the various contours or nooks and crannies of the appliance surface 400. The reflector 420 is designed to direct more energy to the center point of 401 and less to the more nearly focused area to compensate for inverse square losses. Attempting to even out the intensity or energy over the surface. For example; if we broke the half of surface 401 into three sections, 10 percent of the source energy would be directed to the section closest to the source 403, 30 percent would be directed to the middle section and 60 percent would be direct to the third section closet to the center of surface 401. These ratios of energy are exemplary, in alternative embodiments, the amount of energy directed to the nearest, middle, and center sections can be greater or lower depending on a variety of factors. Further, in alternative embodiments, the configuration may be based on fewer or additional zones/sections of disinfection. For example, in alternative embodiments, the cross flow disinfection to the surface may be based on 5, 10, 15, or more different sections from the edge of the surface to the center of the surface. In some embodiments, the configuration of the reflector can provide for a gradient of disinfecting UV light that is highest toward the center of the surface, farthest from the UV source(s) and lowest toward the edge of the surface 401, closest to the UV source(s). Further, the angle, material, and shape, and other properties of reflector (or other disinfection components) can be set to provide a desired amount of UV energy to the respective areas of the touch screen based on data collected about the number and position of screen touches. The angle of the reflector can vary depending on the particular device and its application—for example, for some appliances, some areas of the touch screen are touched more often or have an uneven surface—the reflector for these devices can be specifically configured to direct the ratio of UV light such that those areas that have more touches receive additional UV energy. In other embodiments, the reflector can be configured to provide uniform UV light across the touch screen, accounting for losses that occur as a result of the UV light traveling away from the source. A bezel can mask the side lit UV-C transmissive lens, as depicted in FIG. 4. The reflector 420 can direct the UV light to multiple angles in a low angle that is substantially or almost parallel with the plane of the appliance screen 400. That is, the reflector reflects the UV light toward the touch screen or keypad 400, preventing the UV light from traveling perpendicular to the appliance screen past the bezel.

The appliance 400 can include a controller that can operate the UV source according to a disinfecting protocol. In addition, the appliance can include a controller that is configured to provide decorative control using the same optics. That is, the UV source may be provided with decorative lighting visible to human eyes that can be controlled using the reflector and lens 430 to provide decorative feedback to the user.

Figure 5A:
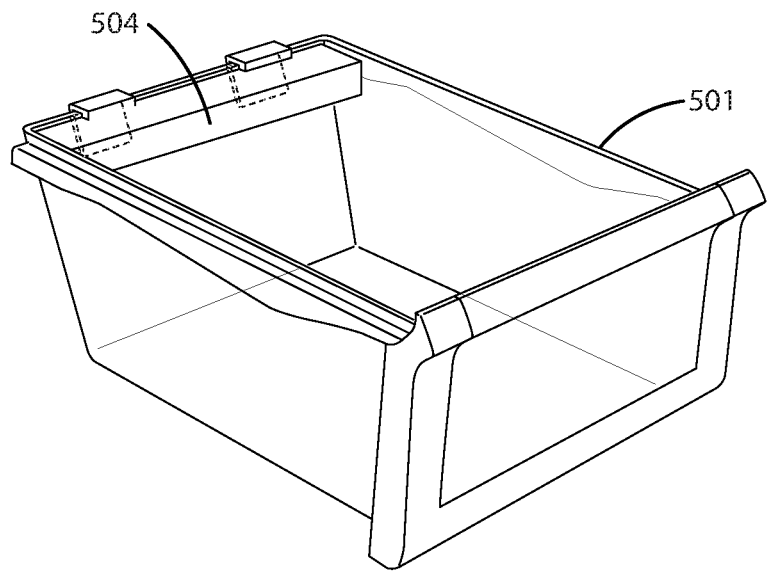
FIGS. 5A-5B illustrate one embodiment of a UV device installed on a crisper drawer.
Figure 5B:
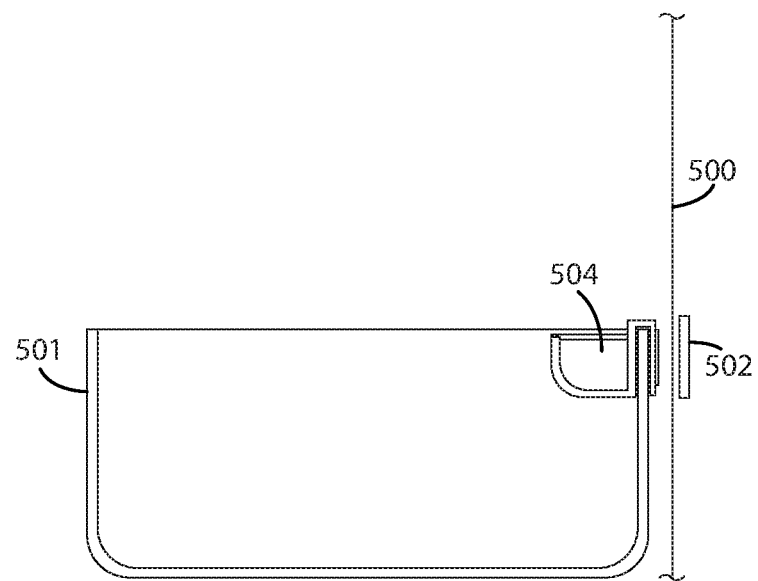

FIG. 5 shows an embodiment of the treatment system that includes a refrigerator appliance having a wall 500 and a crisper drawer 501 for storing fruits, vegetables, or other food. Although not depicted, it should be understood that the refrigerator may include various components and circuitry as described in connection with the first portion 102 depicted in FIG. 1 and the drawer 501 can include various components and circuitry as described in connection with the second portion 104 depicted in FIGS. 1 and 2. A treatment device 504 can be mounted to the drawer 501 for disinfecting the internal surfaces of the drawer as well as its content. The UV lamp length can be roughly the length of the drawer and can be oriented to flood the drawer with both UV-C energy as well as UV-A/B energy. In the current embodiment, the treatment device is snapped on to the top edge of the back of the drawer and provides substantial reach and coverage of UV energy throughout the drawer. In some embodiments, the treatment device 504 may be configured to cooperate with a UV transmissive film lining the internal surface of the drawer 501. For example, in one embodiment, the UV-A/B source and the UV-C source may be positioned to direct UV energy toward the UV transmissive film such that the UV energy travels along the various internal surfaces of the drawer 501 and disperses into the internal area of the drawer.

A wireless power supply 502 can be joined to the appliance wall 500 that provides wireless power through the refrigerator wall 500 to the treatment device 504 installed on the drawer 501. The wireless power link can provide an interlock, which, when broken can halt operation of the treatment device. In response to a user pulling the drawer 501 out, the distance between the wireless power receiving coil in the treatment device 504 and the wireless power supply 502 breaks or otherwise triggers the power interlock and disables the UV source in the treatment device preventing UV exposure to the user of the drawer. When the drawer is pushed back into its closed position, the interlock is reestablished because the coil in the treatment device 504 is slid adjacent to the wireless power supply 502 near the back wall of the refrigerator. Upon re-establishing the power link, the controller in the treatment device can initiate or schedule a disinfection cycle of UV-C energy to disinfect the drawer compartment as well as initiate or schedule a treatment cycle of UV-A/B energy to treat the food stored in the compartment. The cycles can be scheduled periodically to maintain disinfection in the compartment as well as photosynthesis of the food stored in the compartment. The cycles can be scheduled so they do not interrupt each other. In addition, the scheduling may be adapted based on use or other sensor information collected by the system, for example, based on temperature, capacitive touch sensor information, accelerometer information, or information collected from the USB input interface.

Figure 6A:
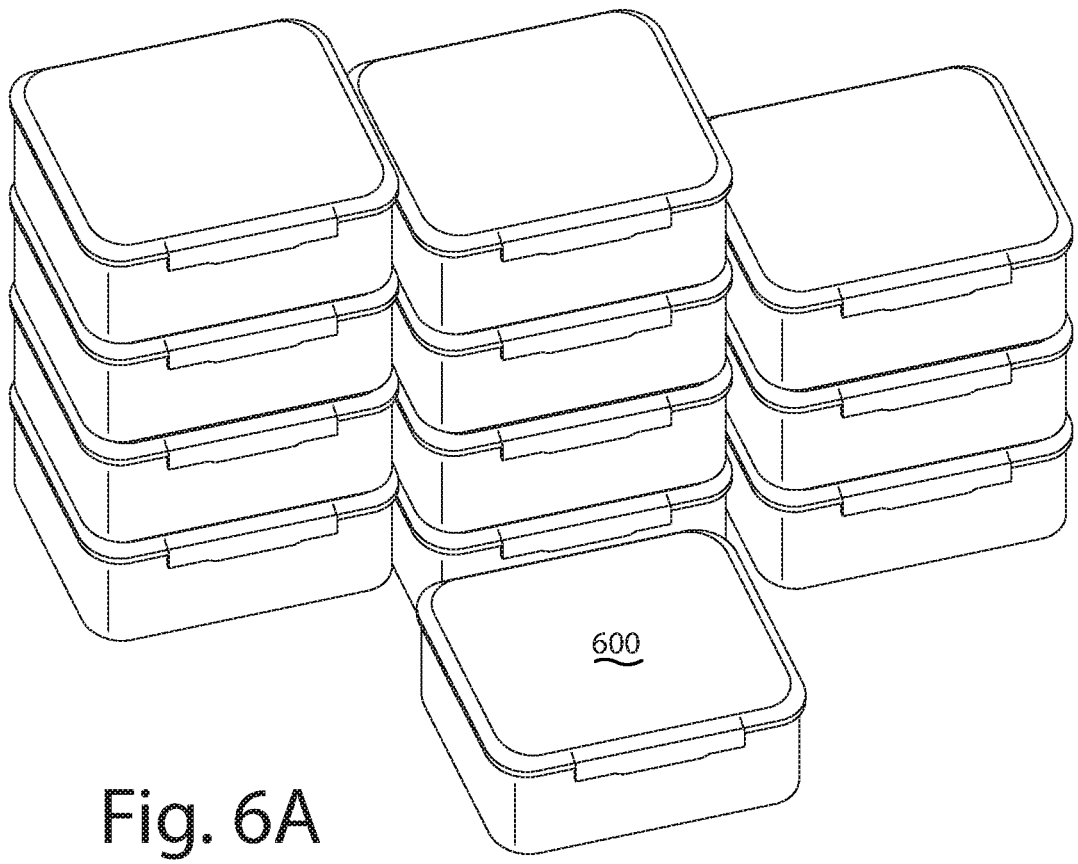
FIG. 6A illustrates one embodiment of a UV food storage container.
Figure 6B:
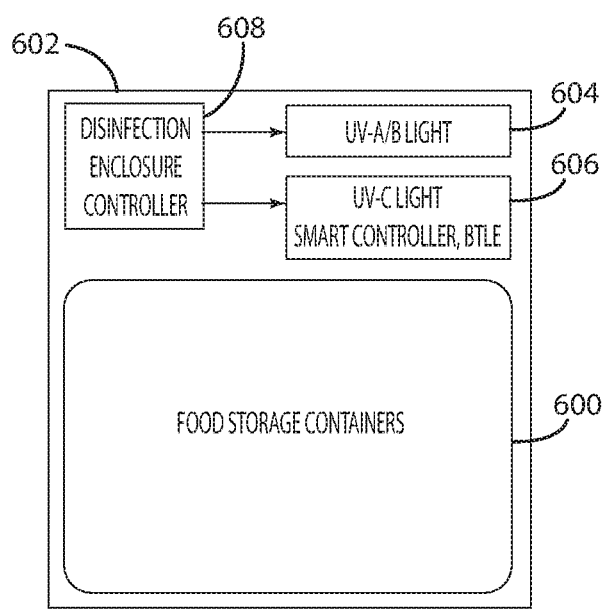
FIG. 6B illustrates one embodiment of a disinfection enclosure including food storage containers.

FIG. 6A shows an example of several UV transparent or UV translucent food storage containers 600 that can be utilized in conjunction with a disinfecting enclosure 602, depicted in FIG. 6B. One example of a disinfecting enclosure is the crisper drawer 501 illustrated in FIG. 5. The UV transparent food storage containers enable the reduction of bacteria and more completely allow food to be exposed to UVC-A/B doses provided by UV sources in a disinfecting enclosure. The disinfection enclosure 602 may include a storage area where one or more food storage containers can be enclosed or stored. The inner surface of the disinfection enclosure may be coated with a UV reflective coating to encourage UV energy to fully envelop and surround the surfaces of the food storage container. The food storage container may be UV transparent enabling the UV-A/B light and the UV-C light to penetrate the walls of the food storage containers and disinfect and treat both the internal and outer surfaces of the food storage containers as well as the content within the food storage container. It may be advantageous to store food in UV transparent containers such as container 600 instead of UV opaque containers. The disinfection enclosure may include a disinfection enclosure controller 608 that controls and drives operation of the UV-A/B light source 604 and the UV-C light source 606. The structure and operation of the disinfection enclosure can mimic operation of the enclosure and treatment device 204 described in connection with FIG. 2. For example, the disinfection enclosure circuitry may include sensor systems, transceivers and antenna circuitry, memory, a power management system, the ability to receiver wireless power from a wireless power transmitter, UV drivers, a behavior feedback display, external lighting drivers and lights, a crypto ID module, as well as essentially any other circuitry or functionality suitable for use in a disinfection enclosure.

The composition and configuration of the thermoplastic composition and the UV reflective material can be selected to provide a composition with desired levels of UV reflectivity, and transmissivity for a desired application. The composition of the thermoplastic composition may also be selected to be cost-effective, and resistant to degradation upon exposure to UV radiation for at least a desired period of time. Utilizing PFA and e-PTFE is a great example of a reflector and UV-C transmissive material. Further details and examples of UV reflective material appropriate for use in the present invention are described in U.S. provisional patent application 62/650,340, entitled Disinfection Behavior Tracking and Ranking, filed on Mar. 30, 2018 to Baarman, and U.S. provisional patent application 62/683,933, entitled Mobile Device Disinfection, filed on Jun. 12, 2018 to Baarman, which are both incorporated by reference in their entirety.

FIGS. 7A-7C illustrate embodiments of a disinfecting appliance handle 700 construction that can be connected to a treatment device, such as the treatment device 204 described in connection with FIG. 2. The handle 700 includes a support member 710 as well as two caps 702 for mounting the handle to an appliance, for example a refrigerator door. The handle may include a two piece transmissive wrap 706, 707 that surrounds the support member 710. The different pieces of the transmissive wrap can have different properties, such as different levels of UV transmissiveness, different colors, polish, or finishes, or different levels of transparency to visible light. In alternative constructions the wrap can be additional or fewer pieces. Fiber optic passages 708 can be provided between the wrap 706 and the support member 710, or elsewhere, such that fiber 726 can be run within the fiber optic passages 708. FIG. 7A shows four fiber optic passageways 708, some embodiments may have a different number of fiber optic passageways or may only utilizes a subset of the passageways. For example, FIG. 7C illustrates a configuration that routes fiber optics through three of the passageways 708. As described in connection with treatment device 113 and object 204, a UV-C source 724 may be provided that couples to the fiber 726 to transmit the UV-C energy to the vicinity of the appliance handle 700. The fiber can be configured, for example by its polish, to permit the scattering and dispersal of the UV-C energy to the entire surface of the handle 700. In addition, the UV transmissive wrap can assist in transferring the UV energy uniformly and completely across the handle surface for effective disinfection. In one embodiment, the construction can include a strong interior support 710 surrounded by a UV transmissive material 706, 707 having a fiber carrying pathway. The handle 700 can be driven with fiber or other sources. The support bar 710 can be a capacitive sense element for detecting touch by coupling the support bar 710 to a capacitive sensor system. The capacitive sense data can be supplied to the appliance control making the handle a human interface device allowing lighting and haptic feedback to the user through the handle.

The treatment device coupled to the handle can include sensors that enable temperature and touch monitoring and allow haptic and visual feedback through lighting control. For example, a capacitive sensor can be coupled to the support member to sense capacitive touch in range of the handle. As another example, a haptic feedback system can be coupled to the support member to provide vibrational feedback.

The treatment device controller can control operation of the treatment device. For example, when the handle is unused, the handle 700 can be disinfected before the next user uses the handle. That is, by way of sensors, the handle can recognize that no user is proximate to the handle and during a period of inactivity disinfect the handle.

As depicted in FIGS. 7A-7C, a UV source 724 can provide UV energy to a UV-C carrying fiber or fibers to distribute UV energy throughout the extruded or molded material for a disinfecting and user feedback enabling surface. The same lighting can enables a decorative opportunity as well adding value and features. The handle 700 can be configured to provide decorative and informative lighting in addition to the disinfection UV light. For example, lighting can be provided in the handle that can indicate disinfection status for ease of use. The appliance handle can provide decorative lighting, usage tracking, and touch tracking functional feedback indication and disinfection. Visible light can be connected simultaneously or selectively coupled to the fiber 726 to provide decorative or feedback lighting—for example the source 724 can be a combined UV/visible source or can be connected to two separate sources. Alternatively, the UV light may be configured to interact with the UV transmissive wrap to provide visible light. In addition, or instead, the handle may be configured with LEDs throughout the handle, which can be controlled by the treatment device to provide decoration and feedback to the user.

Figure 8:
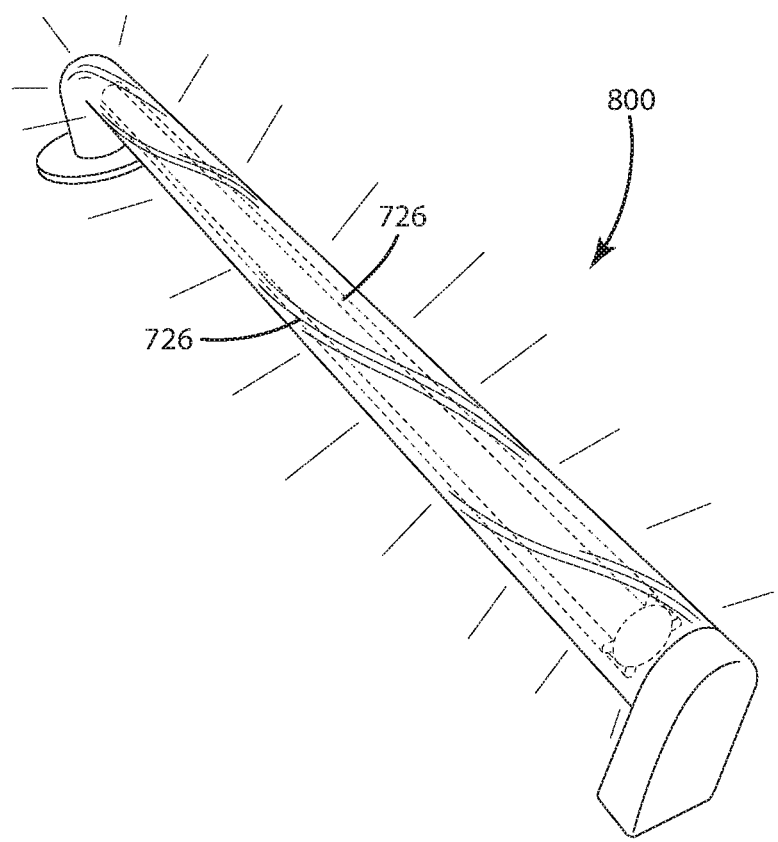
FIG. 8 illustrates an appliance handle with disinfection, user feedback and decorative lighting.

FIG. 8 shows an embodiment of an appliance handle 800 with disinfection and decorative lighting. The lighting can indicate errors, be configured as a theme or scene with other appliances and lighting for decorative lighting. Using RGB LED's or RGB Laser Diodes the user can select millions of decorative colors. The decorative lighting aspect can be programmed to any color or sequence and matched with kitchen lighting or accent details and controlled using interfaces such as Zigbee, Smart Things, Z-wave BTLE, WiFi or other automation communications interfaces.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. An appliance disinfecting system comprising:
   an appliance;
   a moveable storage compartment, wherein at least a portion of the compartment includes UV transmissive material;
   a UV treatment device disposed on the compartment;
   a wireless power supply providing a wireless power link from the appliance to the UV treatment device disposed on the compartment;
   an interlock control system configured to halt operation of the UV treatment device in response to breaking of the wireless power link between the wireless power supply and the UV treatment device.

2. The appliance disinfecting system of claim 1 wherein the moveable appliance compartment is a UVC transmissive food storage system.

3. The appliance disinfecting system of claim 1 wherein the appliance is a refrigerator and the moveable appliance compartment is a crisper drawer.

4. The appliance disinfecting system of claim 1 wherein the UV transmissive material assist UV light transmission throughout the moveable appliance compartment during operation of the UV treatment device.

5. The appliance disinfecting system of claim 1 wherein the UV treatment device includes a UV-C light source configured to disinfect the moveable appliance compartment and a UV A/B light source configured to periodically provide UV-A/B light sufficient in the moveable appliance compartment.

6. The appliance disinfecting system of claim 1 including a user feedback system.

7. The appliance disinfecting system of claim 1 wherein the UV treatment device is mounted to the moveable appliance compartment by a clip.

8. The appliance disinfecting system of claim 1 wherein an inner surface of the moveable appliance compartment is textured to allow scattered reflection.

9. The appliance disinfecting system of claim 1 wherein an inner surface is coated with a UV reflective material that provides dispersion and reflection of UV light.

10. The appliance disinfecting system of claim 1 including a UV transmissive food storage container including a UV transparent material.

\* \* \* \* \*